United States Patent [19]

Meade et al.

[11] Patent Number: 5,478,351
[45] Date of Patent: Dec. 26, 1995

[54] ENDOSCOPIC SURGICAL TOOL WITH HANDLE AND DETACHABLE TOOL ASSEMBLY

[75] Inventors: John C. Meade, Walpole; Philip R. Lichtman, Newton; Erie May, Norfolk, all of Mass.

[73] Assignee: Microsurge, Inc., Needham, Mass.

[21] Appl. No.: 287,069

[22] Filed: Aug. 8, 1994

Related U.S. Application Data

[63] Continuation-in-part of Ser. No. 903,162, Jun. 24, 1992, abandoned, and Ser. No. 4,790, Jan. 14, 1993, abandoned, which is a continuation-in-part of Ser. No. 903,162.

[51] Int. Cl.[6] .................................................... A61B 17/00
[52] U.S. Cl. ............................................ 606/205; 606/174
[58] Field of Search ............................. 606/1, 51, 52, 606/83, 127, 170, 174, 180, 205–211; 128/751–755; 604/22

[56] References Cited

U.S. PATENT DOCUMENTS

| | | |
|---|---|---|
| 2,034,785 | 3/1936 | Wappler . |
| 2,113,246 | 4/1938 | Wappler . |
| 3,147,749 | 9/1964 | Marsh . |
| 4,427,014 | 1/1984 | Bel et al. . |
| 4,522,206 | 6/1985 | Whipple et al. . |
| 4,569,131 | 2/1986 | Falk et al. . |
| 4,881,550 | 11/1989 | Kothe ....................................... 128/751 |
| 4,887,612 | 12/1989 | Esser et al. . |
| 4,896,678 | 1/1990 | Ogawa . |
| 5,052,402 | 10/1991 | Bencini et al. . |
| 5,174,300 | 12/1992 | Balks et al. ............................. 128/751 |
| 5,258,006 | 11/1993 | Rydell et al. . |

FOREIGN PATENT DOCUMENTS

| | | |
|---|---|---|
| 0165472 | 12/1985 | European Pat. Off. . |
| 0308258 | 3/1989 | European Pat. Off. . |
| 0380874 | 8/1990 | European Pat. Off. . |
| 3303335 | 5/1992 | Germany . |

OTHER PUBLICATIONS

Advertisement for "Endo Shears," United States Surgical Corp., (1990).

*Primary Examiner*—Stephen C. Pellegrino
*Assistant Examiner*—William Lewis
*Attorney, Agent, or Firm*—Hamilton, Brook, Smith & Reynolds

[57] ABSTRACT

A surgical tool comprises a detachable tool assembly and tool actuating handle. The tool assembly comprises a tool such as scissors having jaws pivotably mounted via a pivot pin to an inner extension. An outer sleeve around the extension carries a drive pin which engages the tool. The actuating handle retains the inner extension in a fixed position but allows the tool to rotate. Moving a trigger on the actuating handle causes the outer sleeve to translate back and forth over the extension. As the sleeve moves, the drive pin engages the tool to open and close the jaws. The handle is available in a dual-port configuration in which the tool assembly may be inserted in one of two ports.

39 Claims, 10 Drawing Sheets

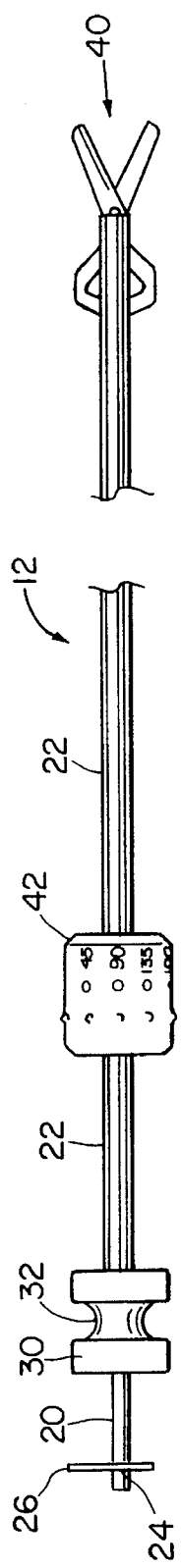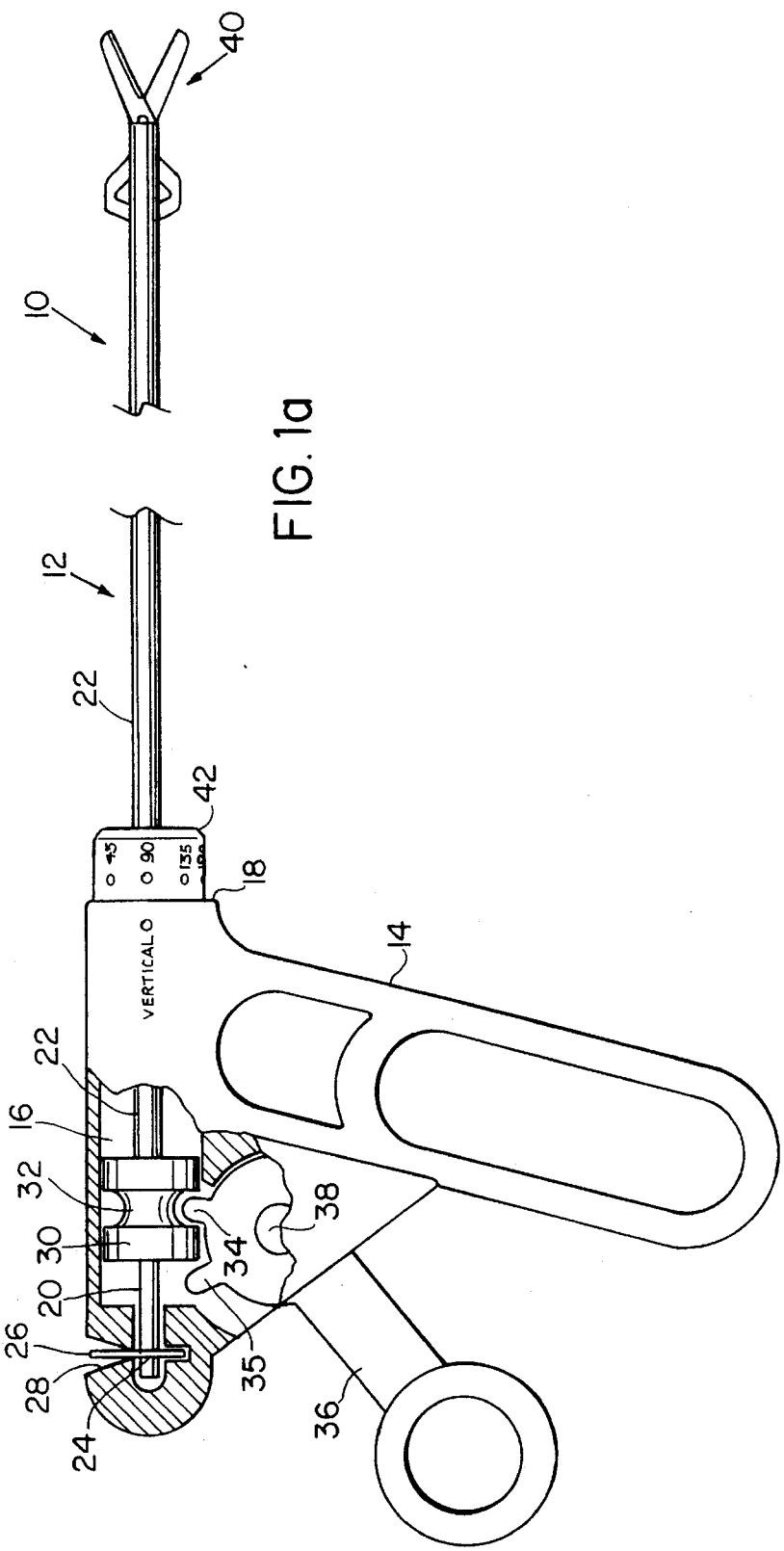

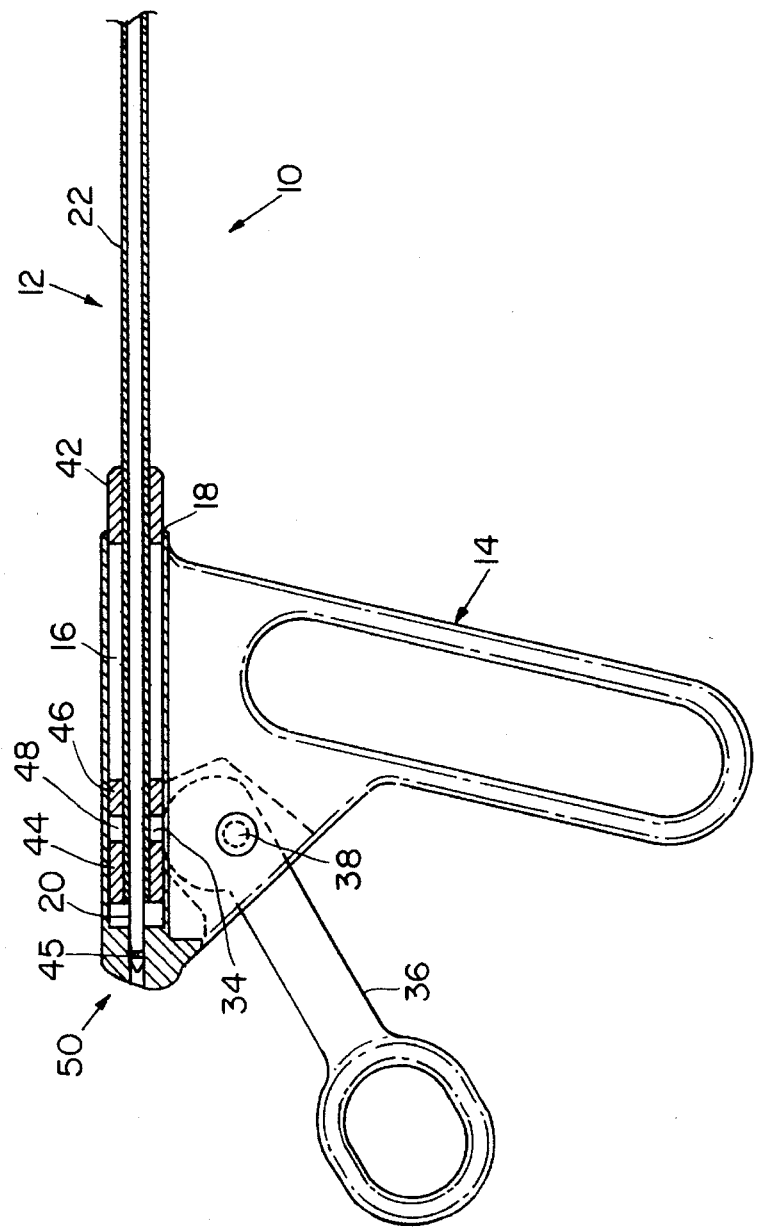
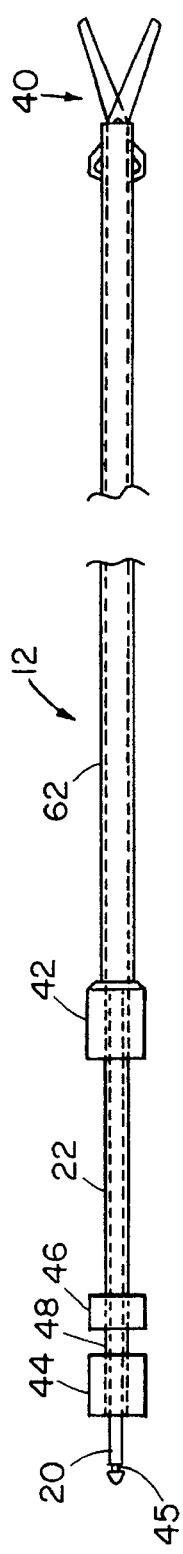
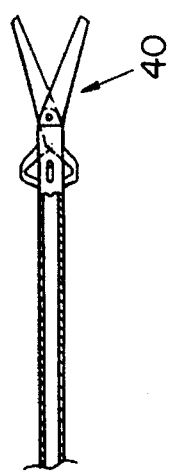
FIG. 2c
FIG. 2a

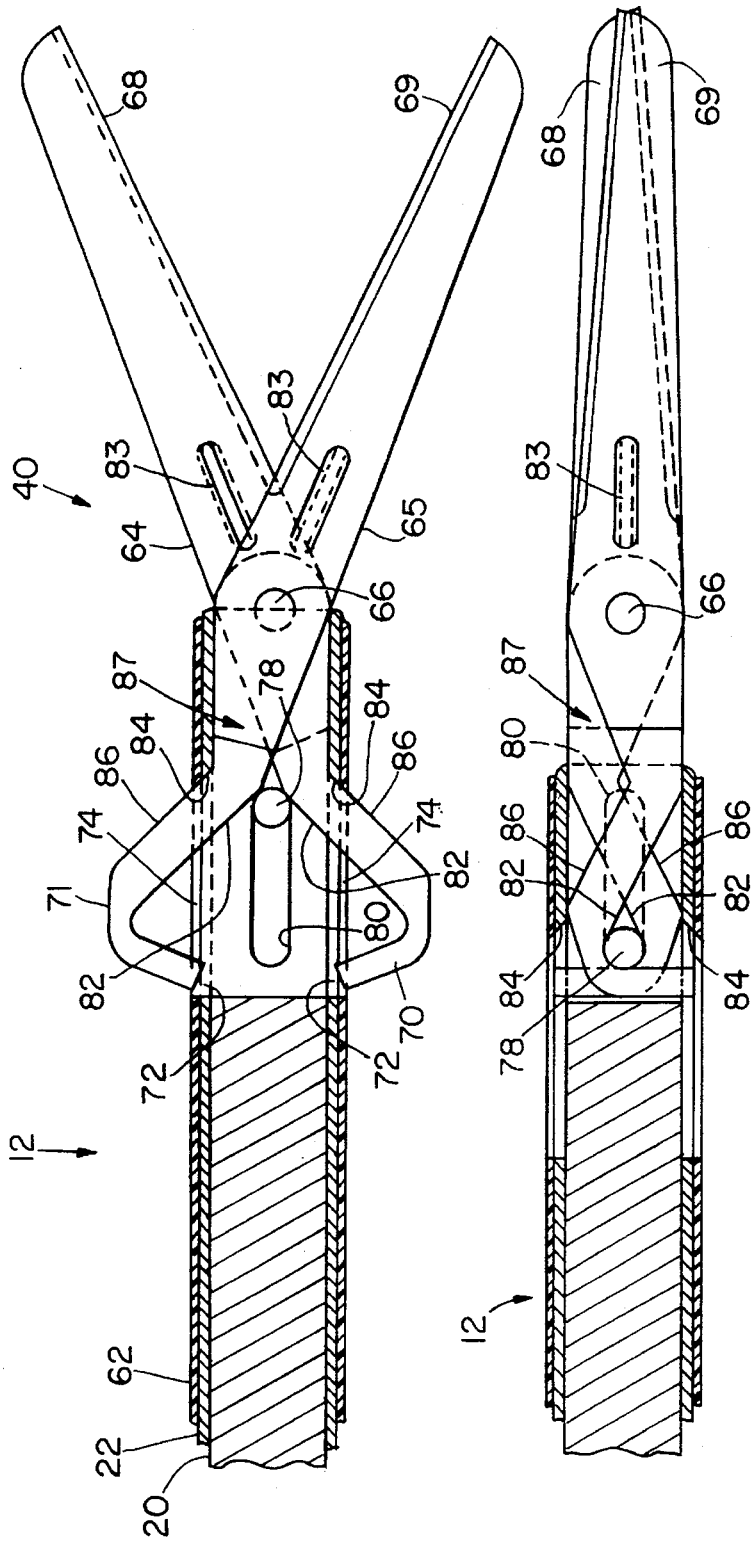

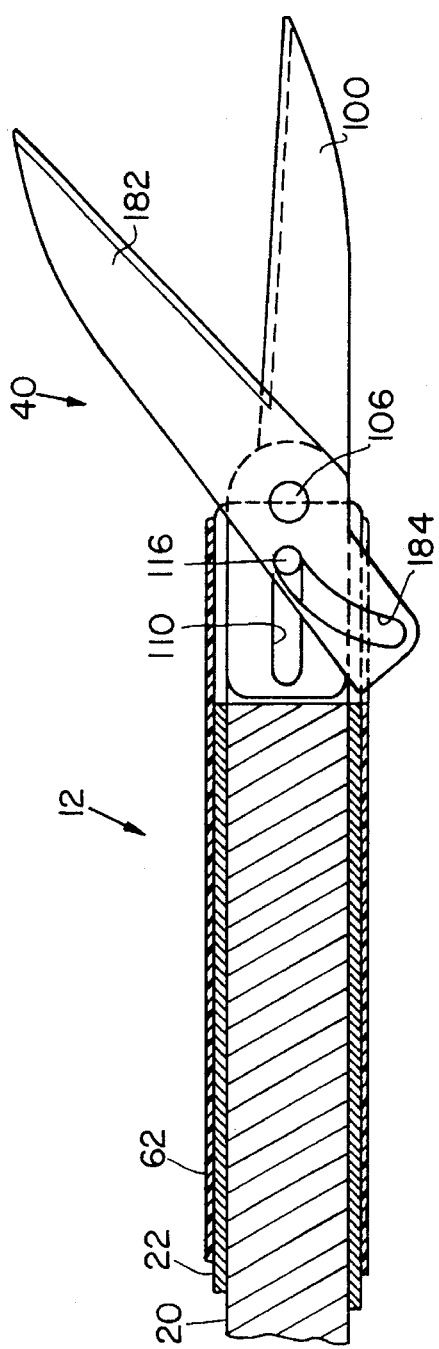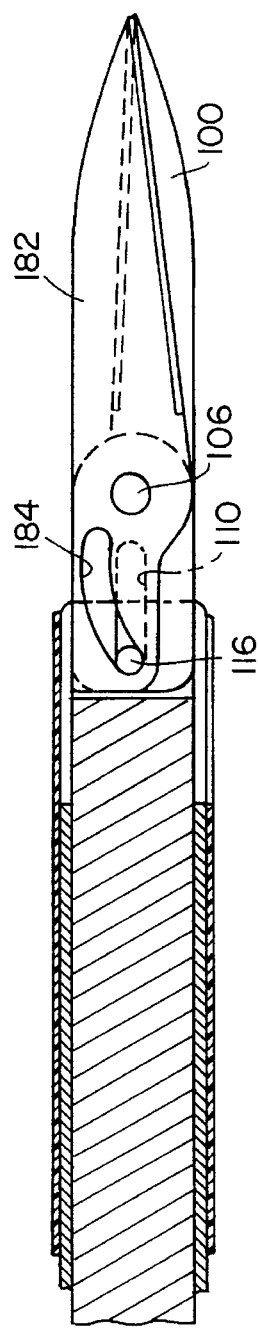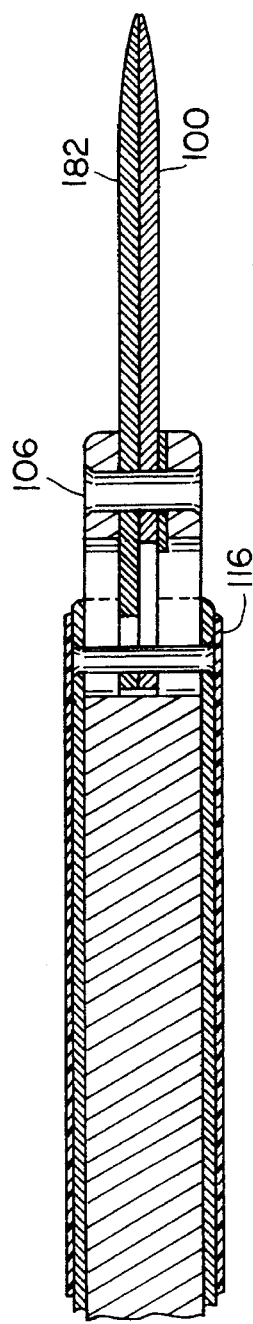

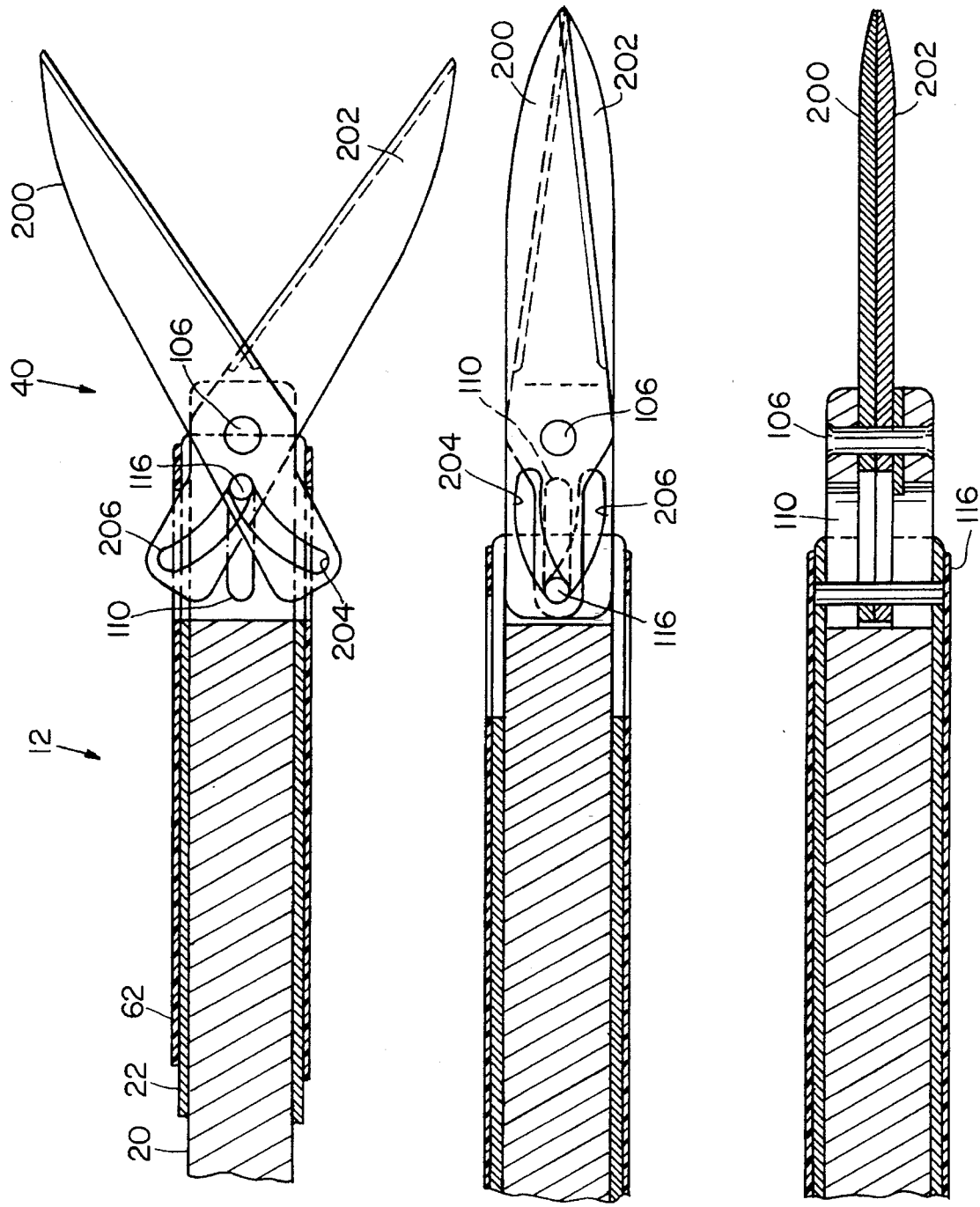

5,478,351

ENDOSCOPIC SURGICAL TOOL WITH HANDLE AND DETACHABLE TOOL ASSEMBLY

RELATED APPLICATION

This application is a continuation-in-part of application Ser. No. 07/903,162 filed on Jun. 24, 1992 and application Ser. No. 08/004,790 filed on Jan. 14, 1993, now abandoned which is a continuation-in-part of application Ser. No. 07/903,162 filed on Jun. 24, 1992, now abandoned. Both applications are incorporated herein in their entirety by reference.

BACKGROUND OF THE INVENTION

Since the late 1980s, endoscopic surgery has been growing in popularity at a very high rate. More and more, procedures which have customarily been performed by making large painful incisions in the patient's body are now being performed by "minimally invasive" or endoscopic methods. It has been estimated that by the year 2000, 40 to 50 percent of all surgeries will be done endoscopically.

Endoscope is the generic term for a viewing tube which can be inserted into the body. In endoscopic surgery, the surgeon makes a hole or portal in the patient's body with a sharp punch-like device called a trocar which is inserted through a sleeve or cannula. The trocar is then removed, leaving the cannula in the portal. The surgeon then inserts desired instruments into the body via the cannula. In many endoscopic procedures, therefore, portals are used to accommodate the instruments needed. These generally include a light source, a TV camera, and surgical tools such as scissors, graspers, dissectors and the like.

With the increase in endoscopic procedures has come an increase in demand for surgical instruments adapted for endoscopic applications. Specifically, the instruments must be small in cross section to minimize trauma of the body. Also, they must be controllable from outside of the body through an extended length. Precise control of tool operation is imperative as any undesirable movement of the tool during surgery can have disastrous results.

Also, in the interest of economics, it is desirable to have disposable tools to avoid the expense of maintenance. For example, rather than sharpening a dull instrument, it can be cost effective to simply replace it. Since only the tool itself needs to be replaced on a regular basis and not the mechanism which controls it, it may be even more cost effective to provide a tool which can be separated from its control mechanism and replaced with a new one.

SUMMARY OF THE INVENTION

An endoscopic surgical tool comprises a tool assembly and a handle assembly. The tool assembly comprises tool jaws pivotably mounted by a pivot such as a pivot pin to the distal end of an extension. A sleeve is positioned about the extension and is translatable relative to the extension to drive the tool jaws between open and closed positions. The proximal end of the tool assembly is inserted into a port in a first portion of the handle assembly. This first portion of the handle assembly has means for retaining the extension against axial movement while permitting rotational movement. The handle also comprises a second portion which is pivotable relative to the first portion to translate the sleeve relative to the extension.

The tool assembly and handle are detachable. The means for retaining provides for release of the extension from the handle. Thus, tool assemblies can be replaced easily and, as a result, can be made disposable. Attachment of the tool assembly to the handle requires only that the tool be inserted into the port and slid back into the handle. When it is forced far enough back, it snaps into place in a retention mechanism in the handle. Also, the tool assembly can be rotated within the handle. This allows for proper positioning of the tool to facilitate the procedure being performed.

In one embodiment, the second portion of the handle engages a groove around the circumference of the sleeve. When the second portion is caused to pivot in relation to the first portion, the sleeve is translated in relation to the extension retained by the first portion. The groove may be provided on a spool attached to the sleeve.

The handle may provide for an electrical connection to the extension. Therefore, the tool allows cautery procedures.

In accordance with another aspect of the invention a dual-port handle comprises two ports for receiving a replaceable tool assembly. The ports are oriented at an angle to each other to provide the surgeon with a choice of preferred tool orientation.

In one embodiment, each of the tool jaws mounted to the extension comprises a tang located at a proximal end of the jaw and a jaw blade at a distal end of the jaw. A pivot such as a pivot pin connects the jaws such that moving the tangs toward each other causes the jaws to move toward the closed position. The pivot pin is attached to the extension. A drive pin engages the jaws to move them toward the open position. The drive pin is attached to the sleeve and is longitudinally positioned between the pivot pin and the proximal end of the tool assembly. The drive pin is positioned between the tangs and engages the tangs such that when the sleeve is translated forwardly toward the distal end of the tool assembly relative to the extension, the tangs are forced outwardly and the jaws move toward the open position. Slots provided in the sleeve engage the tangs such that when the sleeve is translated rearwardly toward the proximal end of the tool assembly relative to the extension, the tangs and thus the jaws move toward the closed position.

In another embodiment, each of the tool jaws comprises a slot at the proximal end of the jaw and a jaw blade at the distal end. A pivot such as a pivot pin pivotably connects the jaws to the extension. A drive pin attached to the sleeve is positioned through the slots. At least one of the slots is angled such that longitudinal translation of the sleeve and drive pin relative to the pivot pin causes the jaws to pivot between the open and closed positions. The drive pin is longitudinally positioned between the pivot pin and the proximal end of the tool assembly. When the sleeve is longitudinally translated rearwardly toward the proximal end of the tool assembly relative to the extension, the jaws move toward the closed position. When the sleeve is translated toward the distal end, the jaws move toward the open position. In this embodiment, one of the jaws may be fixed to the extension so that only the other jaw moves when the sleeve is translated. Also, to reduce friction (by altering the contact angle between the moving parts), the slots in the jaws may be curved.

The surgical tool of the present invention provides distinct advantages over prior art instruments. Most prior art instruments mount the tool to an outer sleeve and actuate it with an inner actuator. In contrast, in the present invention, the tool is mounted to an inner extension. It is an outer sleeve over the extension which actuates the tool. The drive mechanism coupled to the larger diameter sleeve lends to manufacturability of the device, both at the handle and at the tool.

There are prior instruments which mount the tool to an inner member and actuate the tool by moving the inner member longitudinally. In such instruments the cut will be made by a moving tool. In the tool of the present invention, the inner extension is held stationary with respect to the instrument. The outer sleeve is translated longitudinally to actuate the tool. Thus, when the tool is being used, it is held stationary. This allows the surgeon to locate the tool accurately before cutting.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1a is a view of one embodiment of the surgical tool of the present invention.

FIG. 1b is a view of an embodiment of the disposable tool assembly of the present invention.

FIG. 2a is a view of another embodiment of the surgical tool of the present invention.

FIG. 2b is an end view of the embodiment of FIG. 2a.

FIG. 2c is a view of another embodiment of the disposable tool assembly of the present invention.

FIGS. 5a–5c depict an embodiment of the surgical scissors of the present invention.

FIGS. 7a–7c depict another embodiment of the surgical scissors of the present invention.

FIGS. 8a–8c depict another embodiment of the surgical scissors of the present invention.

DETAILED DESCRIPTION OF THE INVENTION

Figure 3:
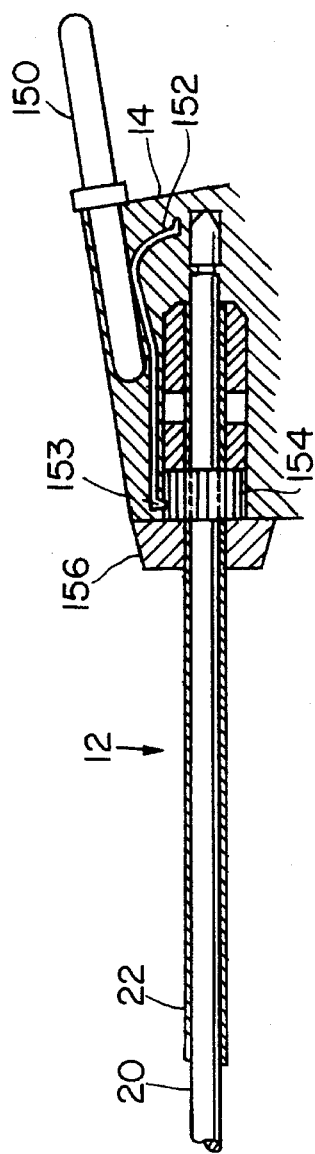
FIG. 3 depicts an embodiment of the electrical connection and rotator of the present invention.

FIG. 1a depicts an embodiment of the surgical tool 10 of the present invention. Tool assembly 12 is removably attached to handle 14. The tool assembly 12 (shown in FIG. 1b) is attached to the handle 14 by inserting its proximal end into space 16 via port 18.

The tool assembly 12 comprises an inner extension 20 within an outer sleeve 22. The outer sleeve 22 can translate back and forth over extension 20. When attaching the tool assembly 12 to the handle 14, the tool assembly 12 is slid to the back of the handle 14. A retaining clip 26 is inserted through space 28 in handle 14 and engages groove 24 in the extension 20 to retain the extension 20 in a fixed axial position relative to the handle 14.

A translation member such as spool 30 is attached to the outer sleeve 22. Groove 32 on the spool 32 engages tab 34 on trigger 36. The trigger 36 is mounted to handle 14 such that it pivots with respect to the handle 14 at pivot 38. When trigger 36 is moved in relation to handle 14, spool 30 moves longitudinally along space 16. Thus, sleeve 22 is caused to translate with respect to extension 20.

In the embodiment of FIGS. 1a and 1b, tool assembly 12 is shown comprising surgical scissors 40. The scissors 40 are mounted to extension 20. Translation of the outer sleeve 22 with respect to the extension 20 causes the scissors 40 to open and close. Therefore, the trigger 36 on the handle 14 is used to control the opening and closing of the scissors 40. As the trigger 36 pivots toward the handle 14, the sleeve 22 translates relative to the extension 20 toward the back (proximal end) of the tool 10. This causes the scissors 40 to close. Moving the trigger 36 away from the handle 14 causes the sleeve 22 to translate forward (toward the distal end of the tool 10). This in turn causes the scissors 40 to open. The scissors 40 will be discussed below in greater detail in connection with FIGS. 5a–5c.

Tool assembly 12 also comprises a rotator knob 42. The rotator knob 42 is attached to the outer sleeve 22. By turning the knob 42, the scissors 40 can be placed in a desired rotational orientation. The rotation of the sleeve 22 causes the scissors 40 to rotate because of the mechanical coupling between the sleeve 22 and the scissors 40 to be discussed in detail below. The rotation is in 45° increments indicated by graduations on the knob 42.

FIG. 1b depicts the tool assembly 12 detached from the handle 14. The tool assembly 12 comprises the inner extension 20, the outer sleeve 22, the spool 30, the retaining clip 26, the rotator knob 42, and the scissors 40. Because of the ease with which the tool assembly 12 can be separated from the handle 14, the tool assembly 12 can be made disposable. Rather than performing maintenance such as sharpening and sterilizing the scissors 40, the entire tool assembly 12 can be discarded and replaced. Thus, the disposable, replaceable tool assemblies 12 can be manufactured and sold separately from the handle assembly 14.

To detach the tool assembly 12 from the handle 14, retaining clip 26 is removed from groove 24 in the extension 20. This allows the entire tool assembly 12 to move freely within space 16. Next, trigger 36 is pulled back to a release position such that it is in line with the axis of the tool assembly 12. As a result, tab 34 disengages from groove 32. Also, the shoulder on the front or distal surface of tab 35 engages the back of the spool 30 to slide the tool assembly 12 toward the front of the handle 14. The tool assembly 12 can then be removed from the handle 14.

To attach a tool assembly 12 to the handle 14, the trigger 36 is again pulled back to the release position. This causes tab 35 to protrude almost perpendicularly into space 16. The tool assembly 12 is inserted into port 18 and is slid toward the back of space 16. The back of spool 30 engages the shoulder on the front or distal surface of tab 35 as the tool assembly 12 is slid back. As this sliding motion continues, trigger 36 pivots so as to allow tab 34 to engage groove 32 in the spool 30. Thus, the two tabs 34 and 35 in combination act as a gear meshing with the back of spool 30 to ensure that when the tool assembly 12 is installed, the trigger 36 will properly actuate the scissors 40. When the tool assembly 12 is fully inserted, retaining clip 26 is inserted into groove 24 in the extension 20 to retain the extension 20 against axial movement.

Figure 2B:
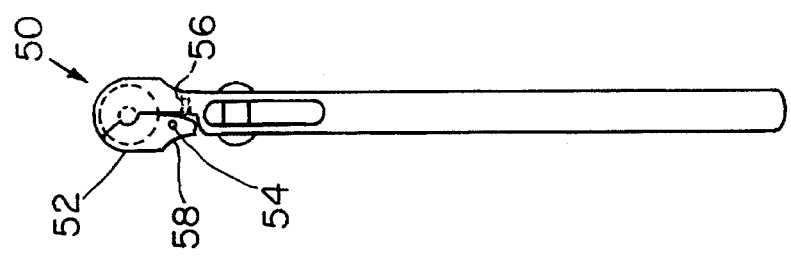

FIG. 2a–2c depict another embodiment of the surgical tool 10 of the present invention. As with the embodiment of FIGS. 1a and 1b, sleeve 22 slides back and forth over extension 20. An insulator cover 62 covers the sleeve 22 between the distal end of rotator knob 42 and the distal end of the sleeve 22. In the preferred embodiment, the insulator cover 62 is attached to the sleeve 22 via a shrink fit. Scissors 40 are attached to the distal end of extension 20. The extension 20 is retained at its proximal end in a fixed axial position relative to the handle 14 and is permitted to rotate about its longitudinal axis. When sleeve 22 is translated with respect to extension 20, scissors 40 open and close.

In this embodiment, spool members 44 and 46 are attached to outer sleeve 22. The spool members are separated from each other along the sleeve 22, forming groove 48 between them. The spool members 44 and 46 and the groove 48 form a translation member used to translate the outer sleeve 22. Tab 34 on trigger 36 engages groove 48. When trigger 36 is moved relative to the handle 14 about pivot 38, sleeve 22 is caused to translate with respect to extension 20 to open or close scissors 40. Rotator knob 42 enables the tool assembly 12 to be rotated to any desired position.

The proximal end of the extension 20 is retained in handle 14 by retention mechanism 50 (see FIG. 2b). The mechanism 50 comprises a tip unlock lever 52, a lever pivot pin 54, and a spring plunger 56. Lever 52 engages groove 45 on extension 20 to retain the extension 20 within the handle 14. To remove the tool assembly 12 from the handle 14, the user presses on thumb area 58 of lever 52. The lever 52 pivots about lever pivot pin 54 against spring plunger 56, causing the upper portion of the lever 52 to move away from the handle 14, thus disengaging from groove 45 on the extension 20. Next, trigger 36 is pulled back to a position approximately in line with the tool assembly 12. This removes tab 34 from groove 48. Finally, the tool assembly 12 is pulled out of the handle 14 via port 18.

To install a tool assembly 12 into the handle 14, the trigger 36 is first pulled back to the release position. The tool assembly 12 is inserted into the handle 14 via port 18, and the trigger 36 is moved to allow the tab 34 to be inserted into groove 48. Finally, the trigger 36 is moved forward to slide the tool assembly 12 toward the back of the handle 14. The tapered end of the extension 20 forces the lever 52 to open against spring plunger 56. The lever 52 closes over the extension 20 when the extension 20 has been forced back far enough to allow the lever 52 to engage the groove 45.

FIG. 3 depicts another embodiment of the tool assembly 12 inserted in a handle. The full handle and trigger are not shown. In this embodiment, electrical connection can be made to the extension 20 to allow for cautery procedures. Electrical terminal 150 is inserted through the back wall of the handle 14. The electrical terminal 150 makes contact with and applies pressure to the electrically conductive spring clip 152. When the tool assembly 12 is installed in the handle 14, the spring clip 152 makes contact with the extension 20. Thus, electrical connection can be made to the extension 20 via terminal 150 and spring clip 152.

In the embodiment shown in FIG. 3, the spring clip 152 also functions to allow "click stop" rotation of the tool assembly 12 within the handle 14. The end 153 of spring clip 152 engages grooves 154 in rotator knob 156 to provide resistance against rotation. As the rotator knob 156 is turned, spring clip 152 acts as a detent, alternating in and out of engagement with successive grooves 154 to provide sufficient retention force against inadvertent rotation of the tool 12.

Figure 4:
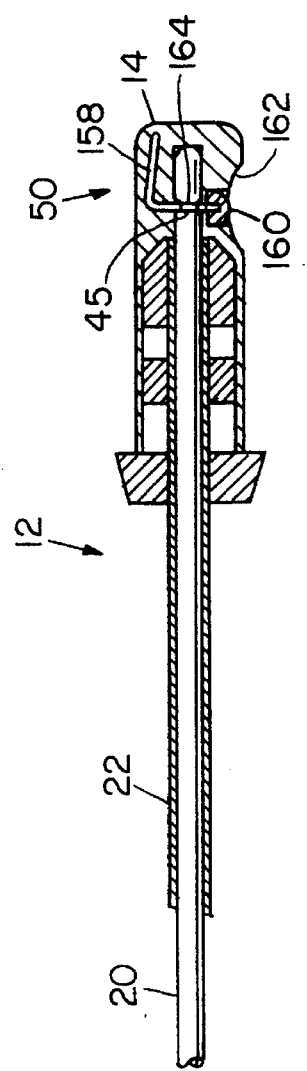
FIG. 4 depicts the retention mechanism of the embodiment of FIG. 3.

FIG. 4 depicts another embodiment of the retention mechanism 50. Retaining clip 158 is connected to button 160 within thumb groove 162. When the button 160 is pressed and released, the retaining clip 158 moves between open and locked positions, respectively. In FIG. 4, the mechanism 50 is shown in the open position. In the open position as shown, the tool assembly 12 is not retained in the handle 14 and can be freely removed. When the button 160 is released, a slot 164 on the retaining clip 158 engages slot 45 on the extension 20 to retain the extension 20. When the tool assembly 12 is installed into the handle 14, the tapered end of the extension 20 moves the retaining clip 158 to the open position. When the tool assembly 12 is moved far enough back into the tool, the slot 164 engages the slot 45 to hold the extension 20 axially.

FIGS. 5a–5c depict an embodiment of the surgical scissors 40 attached to the distal end of the tool assembly 12. FIG. 5a is a view of the scissors 40 in an open position; FIG. 5b is a view of the scissors 40 closed; FIG. 5c is a view rotated 90° from the views of FIGS. 5a and 5b showing the scissors 40 closed. The tool assembly 12 is shown with sleeve 22 around extension 20. An outer insulator cover 62 attached by some means such as shrink fit covers the sleeve 22.

The scissors 40 comprise two jaws 64, 65. The jaws 64, 65 are pivotably connected to each other by pivot pin 66. Pivot pin 66 is attached to the extension 20; thus, the scissors 40 are also attached to the extension 20.

Each of the jaws 64, 65 comprises a blade at its distal end and a tang at its proximal end. In FIG. 5a, jaw 64 comprises blade 68 and tang 70; jaw 65 comprises blade 69 and tang 71. As shown in FIG. 5a, when the scissors 40 are in an open position, the tangs 70, 71 protrude through slots 72 in the sleeve 22 and slots 74 in the insulator cover 62. It can be seen that moving the tangs 70, 71 toward each other will cause the jaws 64, 65 to close. Opening the tangs 70, 71 will cause the jaws 64, 65 to open.

Drive pin 78 is fixed to outer sleeve 22 and is positioned between tangs 70, 71 and passes through slot 80 in the extension 20. As can be seen in FIG. 5a, translation of drive pin 78 toward the distal end of the tool assembly 12 relative to the pivot pin 66 causes the drive pin to engage the inner surfaces 82 of tangs 70, 71. The pin 78 causes the tangs 70, 71 to spread open and thus opens the jaws 64, 65.

To open and close the scissors 40 of the surgical tool 10, the outer sleeve 22 is caused to translate back and forth over the extension 20 by manipulating the handle 14 as described above. To open the scissors 40, the sleeve 22 is translated toward the distal end of the extension 20. Referring again to FIG. 5a, the scissors 40 are shown completely open. The sleeve 22 has been translated to the distal end of the extension 20. Thus, drive pin 78 has forced the tangs 70, 71 apart to cause the jaws 64, 65 to pivot open at pivot pin 66.

FIG. 5b shows the scissors 40 in a closed position. The sleeve 22 has been pulled back (toward the proximal end of the extension 20) over the extension 20. The tangs 70, 71 are closed and, consequently, so are the jaws 64, 65. As the sleeve 22 is moved forward (toward the distal end of the extension 20), the drive pin 78 is also carried forward along slot 80 between the tangs 70, 71. The pin 78 engages the inner surfaces 82 of the tangs 70, 71 to force them apart. As the sleeve 22 moves forward, slots 72 and 74 on the sleeve 22 and cover 62 respectively are also carried forward to allow the tangs 70, 71 to open through the wall of the sleeve 22 and cover 62.

To close the scissors 40, the sleeve 22 is moved back over the extension 20. As the sleeve 22 is pulled back, driving shoulders 84 in the sleeve 22 engage the outer edges 86 of the tangs 70, 71 to squeeze them closed. At the same time, drive pin 78 is pulled back out of the way of the closing tangs 70, 71. The drive pin 78 does maintain contact with the inner surfaces 82 of the tangs 70, 71 to stabilize the jaws 64, 65 as they close. In typical surgical procedures, surgeons commonly use the tips or distal ends of the jaws to do most of the required cutting. In this embodiment of the scissors 40, the distance between the driving shoulders 84 and the pivot pin 66 is selected to maximize the cutting force at the tips of the jaw blades 68, 69. Also, depressions 83 in the jaws 64, 65 provide clearance to allow blades 68, 69 to mesh properly when they close. It should also be noted that if a cautery operation is to be performed, the scissors 40 should remain closed. This will prevent the energized tangs 70, 71 from making undesired contact with tissue. Alternatively, cover 62 may cover the tangs 70, 71 such that they do not make direct contact with tissue when they are open. The cover 62 is of sufficient elasticity to allow the tangs 70, 71 to open and close freely without damage to either the tangs 70, 71 or the cover 62.

FIG. 5c shows the scissors 40 in a closed position. The extension 20 is shown extending through the end of the sleeve 22. The sleeve 22 has been pulled back such that drive pin 78 is at the proximal end of slot 80. Jaws 64, 65 are shown within slot 88 in the extension 20. Pivot pin 66 is shown extending through both jaws 64, 65 and connecting to the extension 20 at opposite sides of slot 88. In this embodiment, spring washer 90 maintains pressure on jaws 64, 65 to keep them tightly mounted to the extension 20 within slot 88. The spring washer 90 eliminates undesirable movements of loosely mounted jaws.

Referring to FIG. 5c, it can be seen that jaws 64, 65 are thinner toward their proximal ends. The jaws 64, 65 are made thinner approximately at area 87 as shown in FIG. 5c. The reason for the step in thickness of the jaws 64, 65 is to provide optimum opposing pressure between the jaw blades 68, 69 as they close. The jaws 64, 65 are made such that when they are placed together in a closed position, they tend to make contact only at their proximal and distal ends. Also, they tend to bow away from each other in the area indicated by reference number 87. When installed in a tool assembly 12, the jaws 64, 65 are squeezed together at area 87. This biases the jaws 64, 65 toward each other as they are opened and closed. This bias allows the jaw blades 68, 69 to cut more effectively. The jaws 64, 65 are thinner toward their proximal ends to provide a spring effect to maintain the ideal pressure between the blades 68, 69.

Figure 6A:
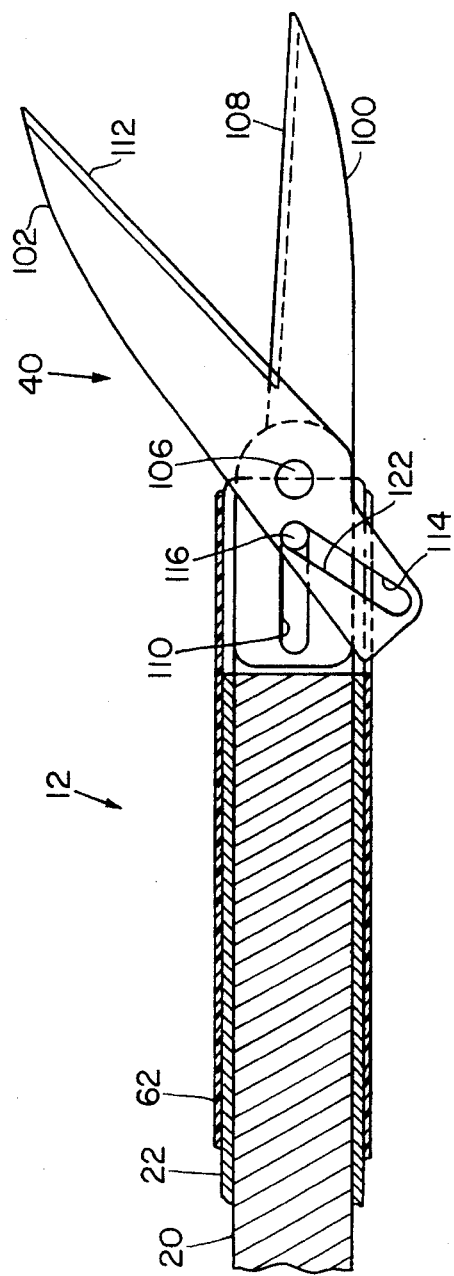
FIGS. 6a–6c depict another embodiment of the surgical scissors of the present invention.
Figure 6B:
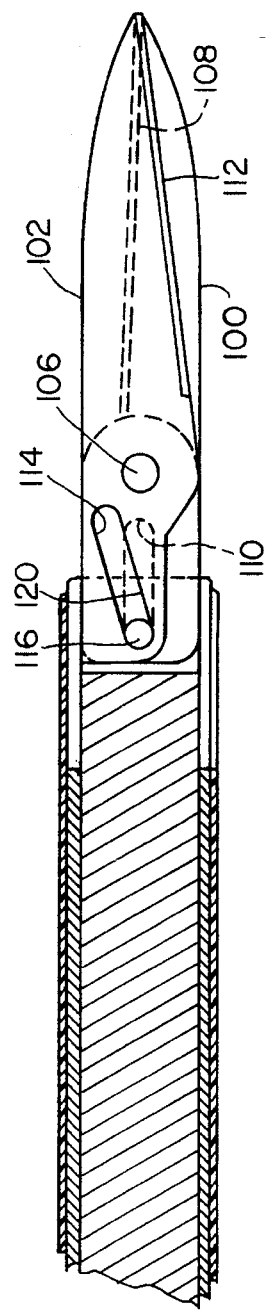
Figure 6C:
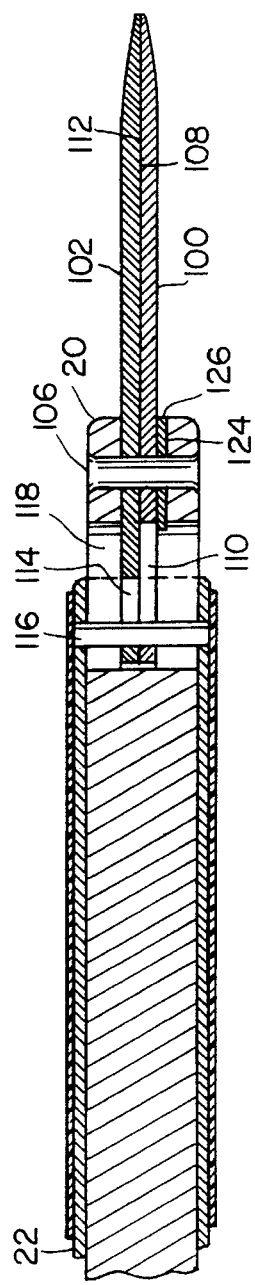

FIGS. 6a–6c depict another embodiment of the surgical scissors 40 of the present invention. FIG. 6a is a view of the scissors 40 in an open position; FIG. 6b is a view of the scissors 40 closed; FIG. 6c is a view rotated 90° from the views of FIGS. 6a and 6b showing the scissors 40 closed. As with the previous embodiment, sleeve 22 slides over extension 20 to open and close the scissors 40. The sleeve 22 is covered with an insulator cover 62 such as by shrink fit.

The scissors 40 comprise two jaws 100, 102. The jaws 100, 102 are mounted to the extension 20 by pivot pin 106. They pivot with respect to each other about the pivot pin 106. In this embodiment, jaw 100 does not pivot with respect to the extension 20 and sleeve 22. Jaw 100 is stationary because slot 110 in jaw 100 is in line with the line of motion of drive pin 116. Thus, translation of sleeve 22 over extension 20 does not induce the jaw 100 to pivot. To close and open scissors 40, jaw 102 pivots toward and away from jaw 100.

Each of the jaws 100, 102 comprises a blade at its distal end and a slot at its proximal end. Jaw 100 comprises blade 108 and slot 110; jaw 102 comprises blade 112 and slot 114. When the jaws 100, 102 are mounted to the extension 20 by pivot pin 106, slots 110 and 114 can be made to overlap to allow drive pin 116 to be inserted through the slots 110, 114.

Drive pin 116 is mounted to outer sleeve 22 as shown in FIG. 6c. As the sleeve 22 is translated back and forth over the extension 20, the drive pin 116 moves back and forth within slots 110, 114 and clearance slot 118 in extension 20. Slots 110 and 118 are oriented along the longitudinal axis of the tool assembly 12. Thus they provide clearance to allow drive pin 116 to move. Slot 114, on the other hand, is oriented such that when drive pin 116 is moved, it engages the inner walls of the slot 118 to cause jaw 102 to pivot about pivot pin 106.

FIG. 6b shows the scissors 40 in a closed position. To open the scissors 40, outer sleeve 22 is translated toward the distal end of the extension 20. As the sleeve 22 moves forward, drive pin 116 is carried with it. The drive pin 116 engages inner surface 120 of slot 114. The force on the surface 120 causes the jaw 102 to pivot about pivot pin 106 toward the open position.

FIG. 6a shows the scissors 40 in the open position. To close the scissors 40, sleeve 22 is translated back toward the proximal end of the extension 20. As the sleeve 22 moves, the drive pin 116 is carried back with it. The pin 116 engages inner surface 122 of slot 114 to cause the jaw 102 to pivot closed. In this embodiment of the scissors 40, the distance between the drive pin 116 and the pivot pin 66 is chosen to maximize the cutting force at the tips of the jaw blades 108, 112.

FIG. 6c shows the scissors 40 with the jaws 100, 102 closed. Sleeve 22 has been pulled back over extension 20 such that drive pin 116 is at the proximal ends of slots 110, 114. The scissor jaws 100, 102 are mounted within slot 124 in the extension 20. Pivot pin 106 passes through the jaws 100, 102 and is attached at its ends to opposite sides of slot 124. Spring washer 126 ensures that the jaws are held tightly in place.

FIGS. 7a–7c depict another embodiment of the surgical scissors 40 of the present invention. FIG. 7a is a view of the scissors 40 in an open position; FIG. 7b is a view of the scissors 40 closed; FIG. 7c is a view rotated 90° from the views of FIGS. 7a and 7b showing the scissors 40 closed. The scissors 40 of FIGS. 7a–7c are substantially identical in form and function to those of FIGS. 6a–6c with the exception of the slot in the movable jaw.

Referring to FIGS. 7a–7c, slot 184 in movable jaw 182 is curved. The use of a curved slot 184 reduces friction by altering the contact angle between the drive pin 116 and the wall of the slot 184. Thus, a smoother scissor operation is provided.

FIGS. 8a–8c depict another embodiment of the surgical scissors 40 of the present invention. FIG. 8a is a view of the scissors 401 in an open position; FIG. 8b is a view of the scissors 40 closed; FIG. 8c is a view rotated 90° from the views of FIGS. 8a and 8b showing the scissors 40 closed. This embodiment is similar to the embodiment of FIGS. 7a–7c, with certain differences. In the embodiment of FIGS. 8a–8c both jaws 200, 202 move when the outer sleeve 22 is translated over the extension 20. Neither jaw is stationary.

Also, both jaws 200, 202 have curved slots 204, 206.

In the embodiment of FIGS. 8a–8c, jaws 200 and 202 are pivotably mounted to the extension 20 by pivot pin 106. Drive pin 116 is mounted to outer sleeve 22 through curved slots 204, 206. Jaw 200 comprises slot 204, and jaw 202 comprises slot 206.

When the sleeve 22 is translated back over the extension 20, drive pin 116 engages curved slots 204 and 206 to close the jaws 200, 202. When the sleeve 22 is translated forward, the drive pin 116 engages the slots 204, 206 to open the jaws 200, 202.

FIGS. 9–12 depict four different embodiments of a dual-port surgical tool handle 314 of the present invention. The dual-port handle 314 allows the tool assembly 12 to be inserted into either of two ports 318. The ports 318 and 319 are oriented at an angle to each other to allow the surgeon more flexibility in using the tool. The surgeon may choose the handle port to be used based on ease of use, comfort, or any number of factors affecting the surgical procedure to be performed.

The manner of retaining and actuating the tool assembly 12 in the dual-port handle 314 is the same as in the single-port handle 14 in FIG. 1a. A retaining clip 26 is inserted into slot 24 in the end of extension 20. Spool 30 is engaged by a mechanism to translate sleeve 22 back and forth over extension 20. The differences among the four embodiments involve the mechanism used to engage and actuate the tool assembly 12. In another embodiment of the dual-port handle 314, the manner of retaining and actuating the tool assembly 12 is the same as that shown in FIG. 4 and described herein with reference to FIG. 4.

Figure 9B:
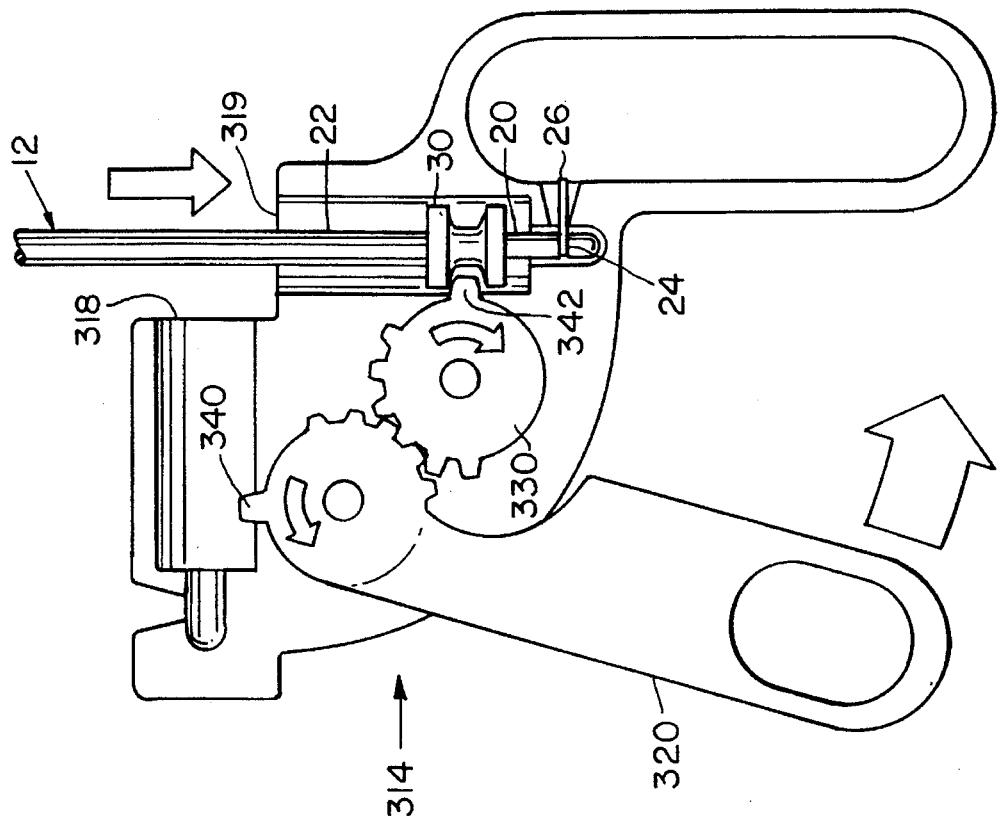
FIGS. 9a–9b depict an embodiment of a dual-port handle in accordance with the present invention.
Figure 9A:
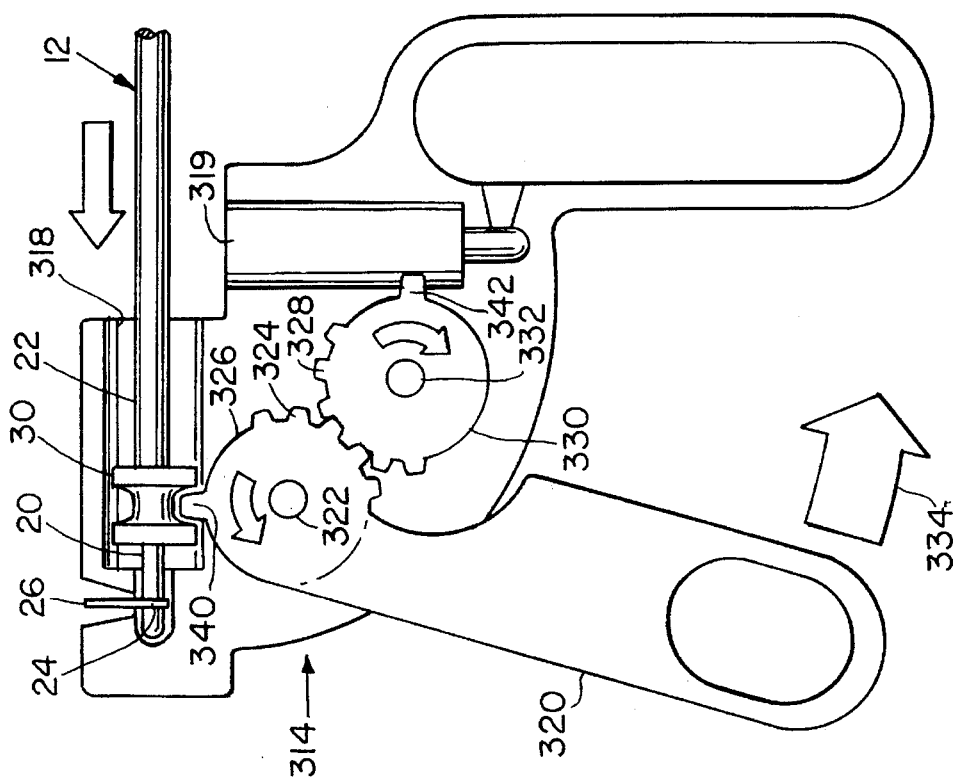

In FIG. 9a, trigger 320 pivots about pin 322. Gear teeth 324 on wheel 326 at the end of trigger 320 mesh with gear teeth 328 on wheel 330. Wheel 330 rotates about pin 332. When trigger 320 is moved in the direction of arrow 334, wheel 326 turns in the counterclockwise direction. At the same time, wheel 330 rotates in the clockwise direction. As the trigger 320 is moved in the opposite direction, the wheels 326 and 330 reverse their directions of rotation.

If the tool assembly 12 is installed in port 318, tab 340 on wheel 326 engages spool 30 to translate sleeve 22 back and forth over extension 20. If the tool assembly 12 is installed in port 319 (see FIG. 9b), tab 342 on wheel 330 engages spool 30 to translate the sleeve 22.

Figure 10:
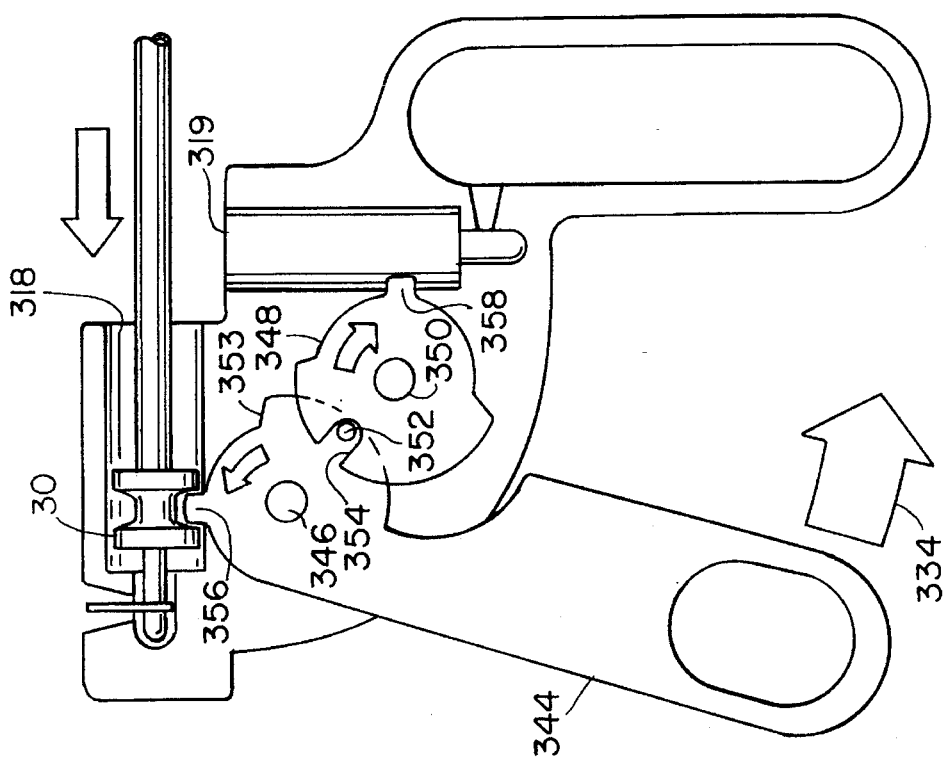
FIG. 10 depicts another embodiment of the dual-port handle in accordance with the present invention.

In FIG. 10, trigger 344 pivots about pin 346. Wheel 348 rotates about pin 350. As trigger 344 is moved in the direction of arrow 334, wheel 353 at the end of trigger 344 rotates in the counterclockwise direction. As wheel 353 rotates, pin 352 fixed to wheel 353 engages slot 354 in wheel 348 to rotate wheel 348 in the clockwise direction. As trigger 344 is moved in the opposite direction, the wheels 353 and 348 reverse their directions of rotation.

If the tool assembly 12 is installed in port 318, tab 356 on wheel 353 engages spool 30 to translate sleeve 22 back and forth over extension 20. If the tool assembly 12 is installed in port 319, tab 358 on wheel 348 engages spool 30 to translate the sleeve 22.

Figure 11:
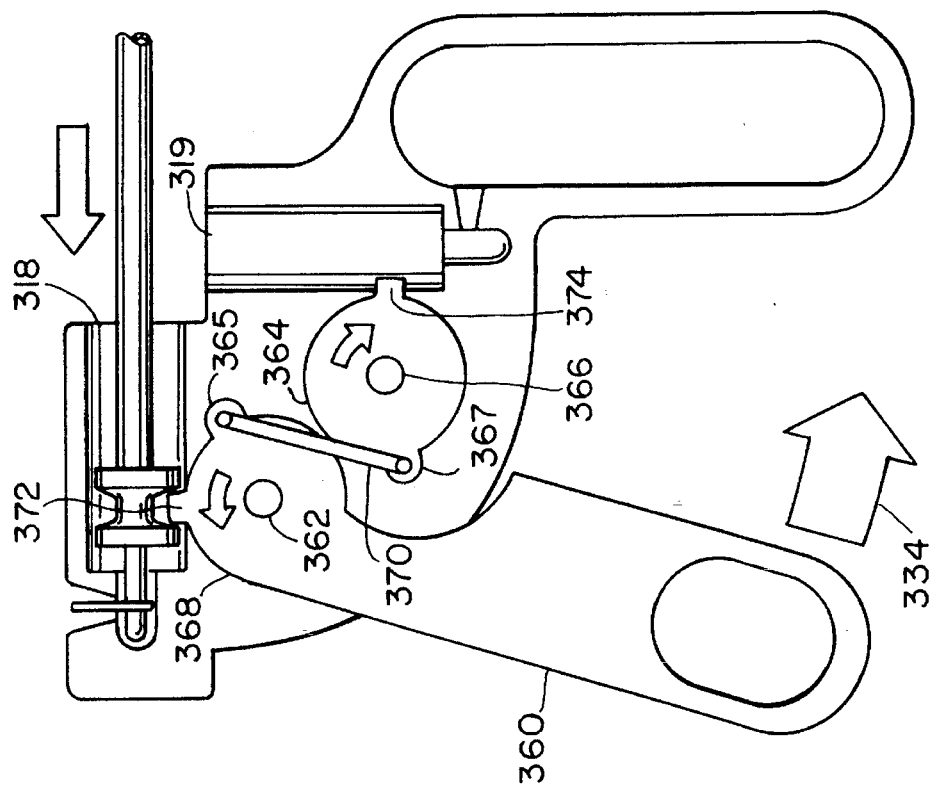
FIG. 11 depicts another embodiment of the dual-port handle in accordance with the present invention.

In FIG. 11, trigger 360 pivots about pin 362. Wheel 364 rotates about pin 366, As trigger 360 is moved in the direction of arrow 334, wheel 368 at the end of trigger 360 rotates in the counterclockwise direction. Wheel 368 is coupled to wheel 364 via connecting pin 370. Connecting pin 370 connects hole 365 on wheel 368 to hole 367 on wheel 364. Consequently, as wheel 368 rotates in the counterclockwise direction, wheel 364 rotates in the clockwise direction. As trigger 360 is moved in the opposite direction, wheels 368 and 364 reverse their directions of rotation.

If the tool assembly 12 is installed in port 318, tab 372 on wheel 368 engages spool 30 to translate sleeve 22 back and forth. If the tool assembly 12 is installed in port 319, tab 374 on wheel 364 engages spool 30 to translate sleeve 22.

Figure 12:
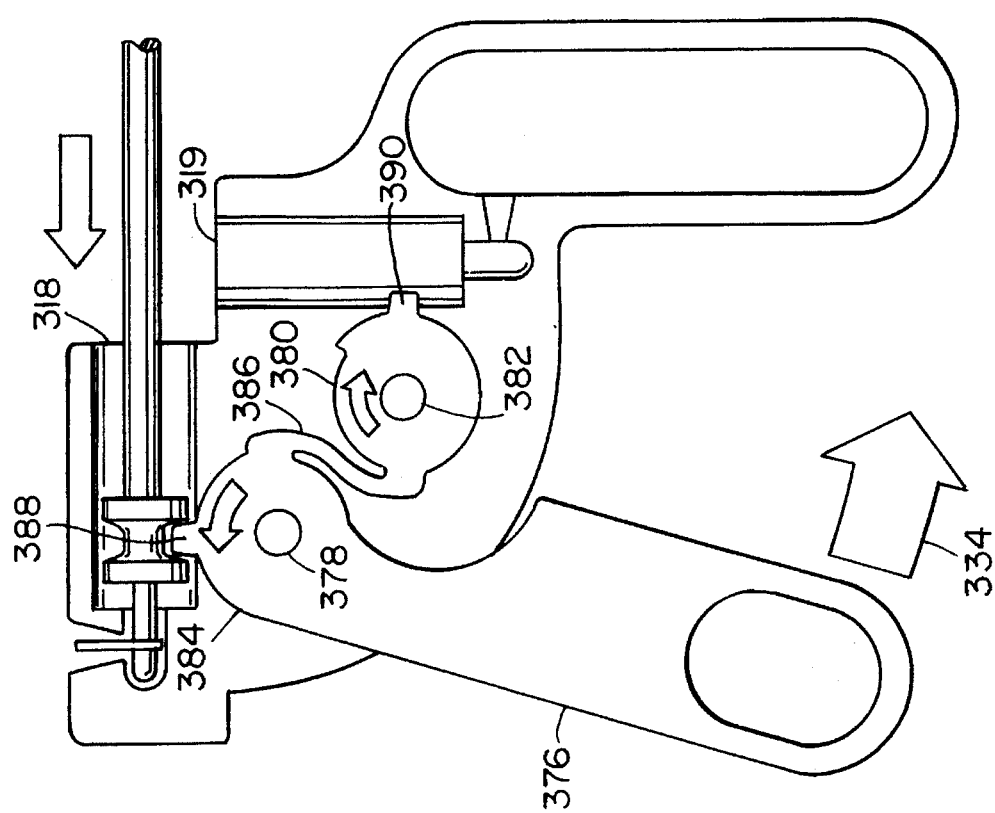
FIG. 12 depicts another embodiment of the dual-port handle in accordance with the present invention.

In FIG. 12, trigger 376 pivots about pin 378. Wheel 380 rotates about pin 382. As trigger 376 is moved in the direction of arrow 334, wheel 384 at the end of trigger 376 rotates in the counterclockwise direction. Wheel 384 is coupled to wheel 380 by flexible coupling member 386. In this embodiment, trigger 376, wheel 384, wheel 380, and flexible coupling member 386 are all made from single piece of material. As a result of the coupling of wheel 384 to wheel 380, as wheel 384 rotates in the counterclockwise direction, wheel 380 rotates in the clockwise direction. As trigger 376 is moved in the opposite direction, wheels 384 and 380 reverse their directions of rotation.

If the tool assembly 12 is installed in port 318, tab 388 on wheel 384 engages spool 30 to translate sleeve 22. If the tool assembly 12 is installed in port 319, tab 390 on wheel 380 engages spool 30 to translate the sleeve 22.

While this invention has been particularly shown and described with references to preferred embodiments thereof, it will be understood by those skilled in the art that various changes in form and details may be made therein without departing from the spirit and scope of the invention as defined by the appended claims. For example, it will be understood that tools other than scissors may be implemented in the tool assembly. These tools include graspers, dissectors, and the like.

We claim:

1. An endoscopic surgical tool comprising:
   a tool assembly comprising:
     an extension;
     tool jaws pivotable relative to each other, at least one jaw being pivotably mounted by a pivot to a distal end of the tool assembly;
     a sleeve about the extension, one of the sleeve and the extension being longitudinally translatable relative to the other to drive the tool jaws to pivot toward open and closed positions; and
     a rotator coupled to the sleeve for rotating the tool assembly About a longitudinal axis of the tool assembly to a desired position; and
   a handle assembly comprising:
     a first portion having a port into which a proximal end of the tool assembly can be inserted and having a retainer engageable with a circumferential groove on the tool assembly to detachably retain the tool assembly, the retainer sliding along and maintaining engagement with the circumferential groove on the tool assembly as the tool assembly is rotated about its longitudinal axis such that the retainer retains the tool assembly while permitting rotation of the tool assembly; and
     a second portion pivotable relative to the first portion to longitudinally translate one of the sleeve and the extension relative to the other.

2. The surgical tool of claim 1 wherein the rotator is graduated to indicate the angle of rotation.

3. The surgical tool of claim 1 further comprising a translation member coupled to the tool assembly having a circumferential second groove engageable by the second portion of the handle for longitudinally translating one of the sleeve and the extension relative to the other.

4. The surgical tool of claim 3 wherein the translation member is coupled to the sleeve.

5. The surgical tool of claim 1 wherein the handle assembly further comprises means for providing an electrical connection to the extension when the tool assembly is retained within the handle assembly.

6. The surgical tool of claim 1 further comprising:
   a pivot pin coupled to the distal end of the extension for mounting the tool jaws; and
   a drive pin coupled to the sleeve, said drive pin engaging the tool jaws to pivot the tool jaws.

7. The endoscopic surgical tool of claim 1 wherein the retainer in the handle assembly comprises a spring biasing the retainer toward engagement with the circumferential groove on the tool assembly such that, as the proximal end of the tool assembly is inserted into the port in the handle assembly, the retainer is forced by the spring into engagement with the circumferential groove on the tool assembly.

8. The endoscopic surgical tool of claim 7 wherein the retainer is forcible against the spring out of engagement with the circumferential groove on the tool assembly to release the tool assembly from the handle assembly.

9. An endoscopic tool assembly for removable attachment to a handle comprising:
   an extension within a sleeve, one of the extension and the sleeve being longitudinally translatable relative to the other and the sleeve and the extension having proximal ends adapted to be longitudinally inserted into a port in the handle and to be retained within the handle;
   at least one pivotable tool jaw coupled to the distal end of the extension and sleeve, the tool jaw pivoting between open and closed positions as one of the extension and the sleeve is longitudinally translated relative to the other;
   a translation member having a circumferential groove engageable by a moveable handle element to longitudinally translate one of the extension and the sleeve relative to the other; and
   a rotator coupled to the sleeve for rotating the endoscopic tool assembly about a longitudinal axis of the tool assembly to a desired position.

10. The tool assembly of claim 9 wherein the translation member comprises a spool coupled to the sleeve.

11. The tool assembly of claim 5 wherein the rotator is graduated to indicate the angle of rotation.

12. The tool assembly of claim 9 further comprising:
    a pivot pin coupled to the distal end of the extension for mounting the tool jaw; and
    a drive pin coupled to the sleeve, said drive pin engaging the tool jaw to pivot the tool jaw.

13. The endoscopic tool assembly of claim 9 further comprising a retention member having a circumferential retention groove engageable by a retaining member within the handle, the retaining member sliding along and maintaining engagement with the retention groove to retain the tool assembly within the handle as the tool assembly is rotated about the longitudinal axis of the tool assembly.

14. An endoscopic surgical tool assembly comprising:
    first and second tool jaws, each tool jaw comprising:
      a tang located at a proximal end of the tool jaw, and
      a jaw blade located at a distal end of the tool jaw;
    a pivot pin pivotably connecting the two jaws such that moving the tangs toward each other causes the jaw blades to pivot toward a closed position, the pivot pin being mounted to an extension; and
    a drive pin engaging the jaws to pivot the jaw blades toward an open position, said drive pin being connected to an outer sleeve around the extension.

15. The surgical tool assembly of claim 14 wherein the drive pin is positioned between the tangs.

16. The surgical tool assembly of claim 15 wherein the tangs are engaged by slots and driving shoulders in the sleeve to pivot the jaws toward the closed position.

17. An endoscopic surgical tool assembly comprising:
    first and second tool jaws, each tool jaw comprising:
      a slot at a proximal end of the jaw, and
      a blade at a distal end of the jaw;
    a pivot pin pivotably connecting the two jaws, said pivot pin being mounted to an extension; and
    a drive pin positioned longitudinally between the pivot pin and the proximal ends of the jaws and engaging the slots to pivot the jaw blades relative to each other, said drive pin being attached to an outer sleeve around the extension.

18. The surgical tool assembly of claim 17 wherein the slots are curved.

19. The surgical tool assembly of claim 17 wherein one of the jaws is fixed to the extension.

20. An endoscopic surgical tool comprising:
    a detachable extended tool assembly; and
    a handle having:
      a port for receiving the tool assembly with axial displacement of the tool assembly;
      a spring biased retaining member for receiving an end of the tool assembly as it is inserted into the handle, said retaining member being caused by the insertion of the tool assembly to retain the tool assembly; and
      a release for releasing the retaining member to release the tool assembly from the handle.

21. A method of using an endoscopic surgical tool, said method comprising:
    providing a surgical tool comprising:
      a tool assembly having a sleeve surrounding an extension and tool jaws pivotably mounted to a distal end of the tool assembly such that translating one of the sleeve and the extension relative to the other causes the tool jaws to pivot between open and closed positions, a rotator being coupled to the sleeve for rotating the tool assembly to a desired position,
      a handle having pivotable first and second portions, said first portion having a port into which a proximal end of the tool assembly is inserted, the port having a retainer for detachably retaining the proximal end of the tool assembly and permitting rotational movement of the tool assembly and rotation of said second portion relative to said first portion causing the sleeve and the extension to translate relative to each other; and
    translating one of the sleeve and the extension relative to the other by rotating the second portion of the handle relative to the first portion of the handle.

22. The method of claim 26 wherein the translating step comprises engaging the second portion of the handle with a circumferential groove on a spool coupled to the sleeve.

23. The method of claim 26 further comprising providing an electrical connection to the extension.

24. A method of using an endoscopic surgical tool, said method comprising:
    providing a surgical tool assembly comprising:
      tool jaws pivotably mounted to a distal end of the tool assembly, a sleeve surrounding an extension such that translating one of the sleeve and the extension relative to the other causes the tool jaws to pivot between open and closed positions, and a spool attached to the sleeve comprising a circumferential groove; and engaging the circumferential groove to translate one of the sleeve and the extension relative to the other.

25. The method of claim 24 further comprising rotating the tool assembly to a desired position.

26. The method of claim 24 wherein the tool assembly comprises:

a pivot pin attached to the distal end of the extension to mount the tool jaws; and a drive pin attached to the sleeve engaging the tool jaws to pivot the tool jaws.

27. An endoscopic surgical tool assembly for removable attachment to a handle comprising:

tool jaws pivotable relative to each other;

an extended jaw actuation device having an inner extension within an outer sleeve, a proximal end for longitudinal insertion into a longitudinal port in the handle, and a distal end to which the tool jaws are mounted, said extension and sleeve being longitudinally translatable relative to each other to pivot the tool jaws;

a retention member fixedly attached to the jaw actuation device comprising a circumferential retention groove engageable by a retaining member within the handle as the actuation device is longitudinally inserted into the handle to retain the jaw actuation device within the handle;

a translation member fixedly attached to the jaw actuation device comprising a circumferential translation groove engageable by a tab within the handle to provide relative longitudinal translation between the extension and the sleeve when the jaw actuation device is retained within the handle; and a rotator for allowing rotation of the tool assembly about a longitudinal axis of the tool assembly as the tool assembly is retained within the handle, the retaining member in the handle sliding along and maintaining engagement with the circumferential retention groove on the retention member and the tab in the handle sliding along the circumferential translation groove on the translation member as the tool assembly rotates.

28. An endoscopic surgical tool assembly for attachment to a handle having a pivotable trigger member comprising:

tool jaws pivotable relative to each other;

an extended jaw actuation device having an inner extension within an outer sleeve, a proximal end for longitudinal insertion into a longitudinal port in the handle, and a distal end to which the tool jaws are mounted, said extension and sleeve being longitudinally translatable relative to each other to pivot the tool jaws;

a retention member fixedly attached to the jaw actuation device comprising a circumferential retention groove engageable by a retaining member within the handle as the jaw actuation device is longitudinally inserted into the handle to retain the jaw actuation device within the handle;

a translation member fixedly attached to the extended jaw actuation device for providing relative longitudinal translation between the inner extension and the outer sleeve, said translation member comprising:

a circumferential translation groove engageable by a tab on the trigger member when the tool assembly is attached to the handle, said tab providing translation motion to the actuation device when the trigger member is caused to pivot; and a proximal surface for engaging a shoulder on the trigger member as the tool assembly is inserted into the handle to rotate the handle such that the tab engages the translation groove; and a rotator for allowing rotation of the tool assembly about a longitudinal axis of the tool assembly as the tool assembly is retained within the handle, the retaining member in the handle sliding along and maintaining engagement with the circumferential retention groove on the retention member and the tab in the handle sliding along the circumferential translation groove on the translation member as the tool assembly rotates.

29. An endoscopic surgical tool comprising:

a tool assembly comprising:

an extension;

tool jaws pivotable relative to each other, at least one jaw being pivotably mounted by a pivot to a distal end of the tool assembly;

a sleeve about the extension, one of the sleeve and the extension being longitudinally translatable relative to the other to drive the tool jaws to pivot toward open and closed positions; and a handle assembly comprising:

a first portion having a port into which a proximal end of the tool assembly can be inserted and having a retainer engageable with a circumferential first groove on the tool assembly to detachably retain the tool assembly, the retainer sliding along and maintaining engagement with the circumferential first groove on the tool assembly as the tool assembly is rotated about a longitudinal axis of the tool assembly such that the retainer retains the tool assembly while permitting rotation of the tool assembly; and a second portion pivotable relative to the first portion, the second portion engaging a circumferential second groove on the tool assembly to longitudinally translate one of the sleeve and the extension relative to the other.

30. The endoscopic surgical tool of claim 29 wherein the circumferential second groove is on a translation member coupled to the sleeve.

31. The endoscopic surgical tool of claim 29 wherein the retainer in the handle assembly comprises a spring biasing the retainer toward engagement with the circumferential first groove on the tool assembly such that, as the proximal end of the tool assembly is inserted into the port in the handle assembly, the retainer is forced by the spring into engagement with the circumferential first groove on the tool assembly.

32. The endoscopic surgical tool of claim 31 wherein the retainer is forcible against the spring out of engagement with the circumferential first groove on the tool assembly to release the tool assembly from the handle assembly.

33. An endoscopic surgical tool comprising:

a tool assembly comprising:

an extension;

tool jaws pivotable relative to each other, at least one jaw being pivotably mounted by a pivot to a distal end of the tool assembly; and a sleeve about the extension, one of the sleeve and the extension being longitudinally translatable relative to the other to drive the tool jaws to pivot toward open and closed positions;

a handle assembly comprising:

a first portion having a port into which a proximal end of the tool assembly can be inserted and having a retainer engageable with a circumferential groove on the tool assembly to detachably retain the tool assembly, the retainer sliding along and maintaining engagement with the circumferential groove on the tool assembly as the tool assembly is rotated about its longitudinal axis such that the retainer retains the tool assembly while permitting rotation of the tool assembly; and a second portion pivotable relative to the first portion to longitudinally translate one of the sleeve and the extension relative to the other; and in the first portion of the handle assembly, means for providing an electrical connection to the tool assembly when the tool assembly is retained within the handle assembly.

34. The endoscopic surgical tool of claim 33 wherein the retainer in the handle assembly comprises a spring biasing the retainer toward engagement with the circumferential groove on the tool assembly such that, as the proximal end of the tool assembly is inserted into the port in the handle assembly, the retainer is forced by the spring into engagement with the circumferential groove on the tool assembly.

35. The endoscopic surgical tool of claim 34 wherein the retainer is forcible against the spring out of engagement with the circumferential groove on the tool assembly to release the tool assembly from the handle assembly.

36. An endoscopic surgical tool comprising:

a tool assembly comprising:
an extension;
tool jaws pivotable relative to each other, at least one jaw being pivotably mounted by a pivot to a distal end of the tool assembly;
a sleeve about the extension, one of the sleeve and the extension being longitudinally translatable relative to the other;
a pivot pin coupled to the distal end of the extension for mounting the tool jaws; and
a drive pin coupled to the sleeve and engaging the tool jaws to pivot the tool jaws toward open and closed positions as one of the sleeve and extension is longitudinally translated relative to the other; and a handle assembly comprising:
a first portion having a port into which a proximal end of the tool assembly can be inserted and having a retainer engageable with a circumferential groove on the tool assembly to detachably retain the tool assembly, the retainer sliding along and maintaining engagement with the circumferential groove on the tool assembly as the tool assembly is rotated about its longitudinal axis such that the retainer retains the tool assembly while permitting rotation of the tool assembly; and a second portion pivotable relative to the first portion to longitudinally translate one of the sleeve and the extension relative to the other.

37. An endoscopic tool assembly for removable attachment to a handle comprising:

an extension within a sleeve, the extension and sleeve being axially translatable relative to each other and having proximal ends adapted to be retained within a handle;

at least one pivotable tool jaw coupled to the distal end of the extension and sleeve, the tool jaw pivoting between open and closed positions as the extension and sleeve are axially translated relative to each other; and a spool attached to the sleeve having a circumferential groove engageable by a moveable handle element to axially translate the extension and the sleeve relative to each other to pivot the tool jaw.

38. A method of using an endoscopic surgical tool, said method comprising:

providing a surgical tool comprising:
a tool assembly having a sleeve surrounding an extension and tool jaws pivotably mounted to a distal end of the tool assembly such that translating one of the sleeve and the extension relative to the other causes the tool jaws to pivot between open and closed positions, and
a handle having pivotable first and second portions, said first portion having a port into which a proximal end of the tool assembly is inserted, the port having a retainer for detachably retaining the proximal end of the tool assembly and permitting rotational movement of the tool assembly and rotation of said second portion relative to said first portion causing one of the sleeve and the extension to translate relative to the other; and translating one of the sleeve and the extension relative to the other by rotating the second portion of the handle relative to the first portion of the handle, the second portion of the handle engaging a circumferential groove on a spool attached to the sleeve.

39. A method of using an endoscopic surgical tool, said method comprising:

providing a surgical tool assembly comprising:
tool jaws pivotably mounted to a distal end of the tool assembly,
a sleeve surrounding an extension such that translating one of the sleeve and the extension relative to the other causes the tool jaws to pivot between open and closed positions,
a pivot pin attached to the distal end of the extension to mount the tool jaws, and
a drive pin attached to the sleeve engaging the tool jaws to pivot the tool jaws; and translating one of the sleeve and the extension relative to the other.

* * * * *

UNITED STATES PATENT AND TRADEMARK OFFICE
CERTIFICATE OF CORRECTION

PATENT NO. : 5,478,351
DATED : December 26, 1995
INVENTOR(S) : John C. Meade, Philip R. Lichtman, Eric May It is certified that error appears in the above-indentified patent and that said Letters Patent is hereby corrected as shown below:

On the Title page of the patent, the spelling of one of the inventors' names should be changed from "Erie May" to --Eric May--.

In Claim 11, column 11, line 42, change "Claim 5" to --Claim 9--.

In Claim 22, column 12, line 54, change "Claim 26" to --Claim 21--.

In Claim 23, column 12, line 57, change "Claim 26" to --Claim 21--.

Signed and Sealed this

Second Day of July, 1996

Attest:

BRUCE LEHMAN

*Attesting Officer*     *Commissioner of Patents and Trademarks*